(12) United States Patent
Harezi et al.

(10) Patent No.: US 7,778,712 B1
(45) Date of Patent: Aug. 17, 2010

(54) BULB APPARATUS

(75) Inventors: Ilonka Harezi, St. Francisville, IL (US); Courtland Reeves, St. Francisville, IL (US)

(73) Assignee: Success by Association, Inc., St. Francisville, IL (US)

( * ) Notice: Subject to any disclaimer, the term of this patent is extended or adjusted under 35 U.S.C. 154(b) by 865 days.

(21) Appl. No.: 10/757,290

(22) Filed: Jan. 13, 2004

Related U.S. Application Data (60) Provisional application No. 60/439,751, filed on Jan. 13, 2003.

(51) Int. Cl.
*A61N 5/06* (2006.01)

(52) U.S. Cl. .................. 607/100; 606/2; 607/88; 313/17; 313/634

(58) Field of Classification Search .......... 606/1–10; 607/88–94; 313/17, 26, 634
See application file for complete search history.

(56) References Cited

U.S. PATENT DOCUMENTS

| | | | | |
|---|---|---|---|---|
| 3,909,736 | A | * | 9/1975 | Huchital et al. ........ 372/71 |
| 4,337,414 | A | * | 6/1982 | Young ................ 315/56 |
| 4,603,277 | A | * | 7/1986 | Imamura et al. ........ 313/25 |
| 5,617,659 | A | * | 4/1997 | Okubo ................ 40/545 |
| 5,680,005 | A | * | 10/1997 | Soules et al. .......... 313/493 |
| 5,717,290 | A | * | 2/1998 | Shaffer .............. 313/545 |
| 5,824,130 | A | * | 10/1998 | Oga et al. ............ 65/276 |
| 5,896,004 | A | * | 4/1999 | Feldman et al. ........ 313/493 |
| 6,433,478 | B1 | * | 8/2002 | Chandler et al. ........ 313/607 |
| 6,696,788 | B2 | * | 2/2004 | Lapatovich et al. ..... 313/634 |

OTHER PUBLICATIONS

Harezi, The Resonance in Residence, © 2002.
Courtland Reeves, Lymph Dysfunction and Its Role in Prostate Cancer, 1995, Explore!, vol. 6, No. 3.
Sky David and Courtland Reeves, Lymph Dysfunction and Its Role Breast Cancer, 1995, Explore!, vol. 6, No. 2.
Light Beam Generator, Prostate Protocol and Good Medicine Confirms Protocol Works!, Date of publication unknown.
Dr. Paul Yanick, Jr., Excerpt from Professionals Guidebook of Quantum Medicine, Date of publication unknown.
Light Beam Generator Tissue Detoxification Family, Date of publication unknown.
Larry Trivieri, Shedding Light on Lymphatic Health, Alternative Medicine Magazine, May 2000.

(Continued)

*Primary Examiner*—Henry M Johnson, III
*Assistant Examiner*—Aaron Roane
(74) *Attorney, Agent, or Firm*—Ice Miller LLP (57) ABSTRACT

A novel bulb and bulb assembly. In an embodiment, the present invention comprises a shell enclosing a hollow interior, and a tube intersecting with the shell such that the ends of the tube reside outside the shell and a portion of the tube resides within the shell. Each intersection of the tube and the shell in this embodiment is accomplished so that any contents of the hollow interior of the shell are sealed within the shell and any contents of the hollow interior of the shell are segregated from any contents of the portion of the tube residing within the shell. This embodiment may further comprise at least one electrode having at least one end terminating inside the shell. This embodiment may further comprise a source of electromagnetic waves positioned such that electromagnetic waves emanating from the source of electromagnetic waves pass through the shell.

19 Claims, 8 Drawing Sheets

OTHER PUBLICATIONS

Lymphatic Therapy Patient Information, Date of publication unknown.

Light Beam Generator Photon Tissue Decongestion Therapy, Date of publication unknown.

Oxygen and Ozone in the Treatment of Cancer, printed from http://www.alkalizeforhealth.net/loxygen/htm on Jan. 7, 2004. Date of publication unknown.

Cancer Killed by Oxygen, printed from http://www.balancedforhealth.com/causeofcancer.htm on Jan. 7, 2004. Date of publication unknown.

Bill Morgan, Scaler Wars—The Brave New World of Scaler Electromagnetics, Date of publication unknown.

Ivars Peterson, Quantum Interference, Dec. 2, 1989.

Yoseph Imry and Richard A. Webb, Quantum Interference and the Aharonov-Bohm Effect, Scientific American, Apr. 1989.

Otto Warburg, The Prime Cause and Prevention of Cancer, Printed from http://www.ozonetherapy.co.uk/articles/warburg_the_prime_cause_of_cancer.htm on Jan. 7, 2004. Date of.

Light Beam Generator Training Manual, Date of publication unknown.

Clinical Results Light Beam Generator ST8 Super Oxygen, Date of publication unknown.

Light Beam Generator User Manual, Sep. 1998.

The Real Science of Non-Hertzian Waves; printed from http://205.243.100.155/frames/non-herzian_waves.html on Apr. 16, 2004; date of.

* cited by examiner

BULB APPARATUS

This non-provisional patent application claims the benefit of U.S. Provisional Application No. 60/439,751, filed Jan. 13, 2003, the disclosure of which is hereby incorporated by reference in its entirety.

BACKGROUND

The second half of the twentieth century saw remarkable advancements in medical technology. Tests, equipment, and procedures such as CAT scans, PET scans, MRI, arthroscopy, laparoscopy, laser eye surgery, and many other tests, equipment, and procedures that became prevalent during that period have contributed to improving the ability of health professionals to diagnose and treat ailments.

It is desired to provide a new medical technology. The desired technology will support the treatment of medical ailments in a non-invasive, non-cytotoxic manner. For example, protein structure in living, healthy tissue is in a state of alignment. This is most evident in the connective tissue that holds the body together where the alignment of collagen fibers is stable. However, protein structures break down as cells die or are damaged. These waste proteins are easily removed by a healthy, functioning lymph system. When the lymph system has become congested or even clogged and it can no longer efficiently flush these wastes, these useless proteins become trapped in the interstitium (the area between the living cells in connective tissue). Such non-functional proteins have the same properties of attraction as functioning proteins, though as they organize, their structures are completely random and characterized by instability. This is called fibrotic condition of the interstitium. The instability of these non-functional proteins causes them to attract water and hold it via electrical bonding, resulting in swelling and further congestion—a condition known as edema. With a clogged lymphatic system continuing to fill with waste proteins and other toxins, organs lose their ability to remove wastes through the lymph system. The result can be the development of many different kinds of pathologies in the body. It is desired to provide a medical technology that effectively and non-invasively treats lymphedema by separating the non-functioning proteins and releasing the retained water, thus restoring natural lymph fluidity and greatly enhancing the delivery of waste material to the organs and nodes responsible for waste elimination.

In another example, the medical benefits of ozone have been studied for many years. The Max Planck Institute in Germany developed a premise of injecting ozone into cancerous tumors of critical care patients. When ozone was injected, it was observed that the cancer disease was devitalized, as cancer cells cannot live in an oxygenated environment. Ozone therapies are available in many countries. However, there are concerns about toxicity of ozone. As a result, the United States Food and Drug Administration has never approved ozone generators or ozone gas for treating any medical condition. It is desired to provide a medical technology that permits the non-invasive delivery of the benefits of ozone treatment, but avoids the toxic side effects.

SUMMARY

The present invention comprises a novel bulb and bulb assembly. The bulb and bulb assembly of the present invention have applications in the treatment of medical ailments in a non-invasive and non-cytotoxic manner. In an embodiment, the present invention can be adapted for the treatment of, or symptom reduction in, connective tissue disorders such as, for example, lymphedema. In an embodiment, the present invention can be adapted to deliver the benefits of ozone therapy to treat an ailment such as cancer, while eliminating the need for the ingestion or infusion of ozone. Such embodiments of the present invention can be used in combination with other medical protocols.

In an embodiment, the present invention comprises a bulb. The bulb of this embodiment comprises a shell enclosing a hollow interior; and a tube having a first open end and a second open end and a continuous pathway communicating between the first open end and the second open end, the tube intersecting with the shell such that the first open end and the second open end reside outside the shell and a portion of the tube between the first open end and the second open end resides within the shell. Each intersection of the tube and the shell in this embodiment is accomplished so that any contents of the hollow interior of the shell are sealed within the shell and any contents of the hollow interior of the shell are segregated from any contents of the portion of the tube residing within the shell. The bulb of this embodiment further comprises at least one electrode having at least one end terminating inside the shell. In an implementation of this embodiment, the portion of the tube residing within the shell is configured as a spiral comprising a plurality of concentric turns. This implementation can be adapted so that each successive concentric turn of the plurality of concentric turns decreases in diameter.

In an embodiment, the present invention comprises a bulb. The bulb of this embodiment comprises a shell enclosing a hollow interior that is filled with a gaseous matter; and a tube having a first open end and a second open end and a continuous pathway communicating between the first open end and the second open end, the tube intersecting with the shell such that the first open end and the second open end reside outside the shell and a portion of the tube between the first open end and the second open end resides within the shell. Each intersection of the tube and the shell in this embodiment is accomplished so that any contents of the hollow interior of the shell are sealed within the shell and any contents of the hollow interior of the shell are segregated from any contents of the portion of the tube residing within the shell. The bulb of this embodiment further comprises at least one electrode having at least one end terminating inside the shell. In an implementation of this embodiment, the gaseous matter filling the shell comprises a mixture of noble gasses.

In an embodiment, the present invention comprises a bulb. The bulb of this embodiment comprises a shell enclosing a hollow interior that is filled with a gaseous matter; and a tube having a first open end and a second open end and a continuous pathway communicating between the first open end and the second open end, the tube intersecting with the shell such that the first open end and the second open end reside outside the shell and a portion of the tube between the first open end and the second open end resides within the shell, wherein the portion of the tube residing within the shell encloses a flowing substance. Each intersection of the tube and the shell in this embodiment is accomplished so that any contents of the hollow interior of the shell are sealed within the shell and any contents of the hollow interior of the shell are segregated from any contents of the portion of the tube residing within the shell. Accordingly, the flowing substance enclosed in the tube does not intermingle with the gaseous matter that is outside the tube but inside the shell. In this embodiment, the flowing substance enclosed in the tube may comprise ozone, a medicine, or another substance used to treat an ailment suffered by a biological system.

In an embodiment, the present invention comprises a bulb. The bulb of this embodiment comprises a shell enclosing a hollow interior; and a tube having a first open end and a second open end and a continuous pathway communicating between the first open end and the second open end, the tube intersecting with the shell such that the first open end and the second open end reside outside the shell and a portion of the tube between the first open end and the second open end resides within the shell. The bulb of this embodiment of the present invention further comprises a source of electromagnetic waves, the source of electromagnetic waves positioned such that electromagnetic waves emanating from the source of electromagnetic waves pass through the shell. In an implementation of this embodiment, the source of electromagnetic waves comprises a coil.

In an embodiment, the present invention comprises a bulb. The bulb of this embodiment comprises a shell enclosing a hollow interior; and a tube having a first open end and a second open end and a continuous pathway communicating between the first open end and the second open end, the tube intersecting with the shell such that the first open end and the second open end reside outside the shell and a portion of the tube between the first open end and the second open end resides within the shell, wherein the portion of the tube residing within the shell encloses a flowing substance. The bulb of this embodiment further comprises at least one electrode having at least one end terminating inside the shell. The bulb of this embodiment of the present invention further comprises a source of electromagnetic waves, the source of electromagnetic waves positioned such that electromagnetic waves emanating from the source of electromagnetic waves pass through the shell. In an aspect of this embodiment of the present invention, the source of electromagnetic waves is energized by an alternating electrical current, and a voltage is applied to the electrode.

In an embodiment the present invention comprises a method for treating a biological system. According to the method of this embodiment at least one bulb is provided, each of the at least one bulbs comprising a shell enclosing a hollow interior, a tube having a first open end and a second open end and a continuous pathway communicating between the first open end and the second open end, the tube intersecting with the shell such that the first open end and the second open end reside outside the shell and a portion of the tube between the first open end and the second open end resides within the shell, the intersections of the tube and the shell being accomplished such that any contents of the hollow interior of the shell are sealed within the shell and any contents of the hollow interior of the shell are segregated from any contents of the portion of the tube residing within the shell, at least one electrode having at least one end terminating inside the shell, and a source of electromagnetic waves outside the shell, the source of electromagnetic waves positioned such that electromagnetic waves emanating from the source of electromagnetic waves pass through the shell. A substance is caused to flow through the portion of the tube residing within the shell in each of the at least one bulbs. Each source of electromagnetic waves is caused to emit electromagnetic waves. A voltage is applied to the at least one electrodes of each of the at least one bulbs. In an aspect of this embodiment, the present invention further comprises the step of placing at least one of the at least one bulbs in proximity to a biological system.

In an embodiment, the present invention comprises a bulb. The bulb of this embodiment comprises a shell enclosing a hollow interior; a plurality of tubes, each having a first open end and a second open end and a continuous pathway communicating therebetween, each of the plurality of tubes intersecting with the shell such that the first open end and the second open end of each of the plurality of tubes reside outside the shell and a portion of each of the plurality of tubes resides within the shell, each the intersection of one of the plurality of tubes and the shell being accomplished such that any contents of the hollow interior of the shell are sealed within the shell and any contents of the hollow interior of the shell are segregated from any contents of the portion of each of the plurality of tubes residing within the shell; and at least one electrode, each of the at least one electrodes having at least one end terminating inside the shell.

BRIEF DESCRIPTION OF THE DRAWINGS

The features and advantages of this invention, and the manner of attaining them, will be more apparent and better understood by reference to the following descriptions of embodiments of the invention, taken in conjunction with the accompanying drawings, wherein.

DESCRIPTION

The present invention comprises a novel bulb and bulb assembly. The bulb and bulb assembly of the present invention have applications in the treatment of medical ailments in a non-invasive and non-cytotoxic manner. In an embodiment, the present invention can be adapted for the treatment of, or symptom reduction in, connective tissue disorders such as, for example, lymphedema. In an embodiment, the present invention can be adapted to deliver the benefits of ozone therapy to treat an ailment such as cancer, while eliminating the need for the ingestion or infusion of ozone. Such embodiments of the present invention can be used in combination with other medical protocols.

Figure 1A:
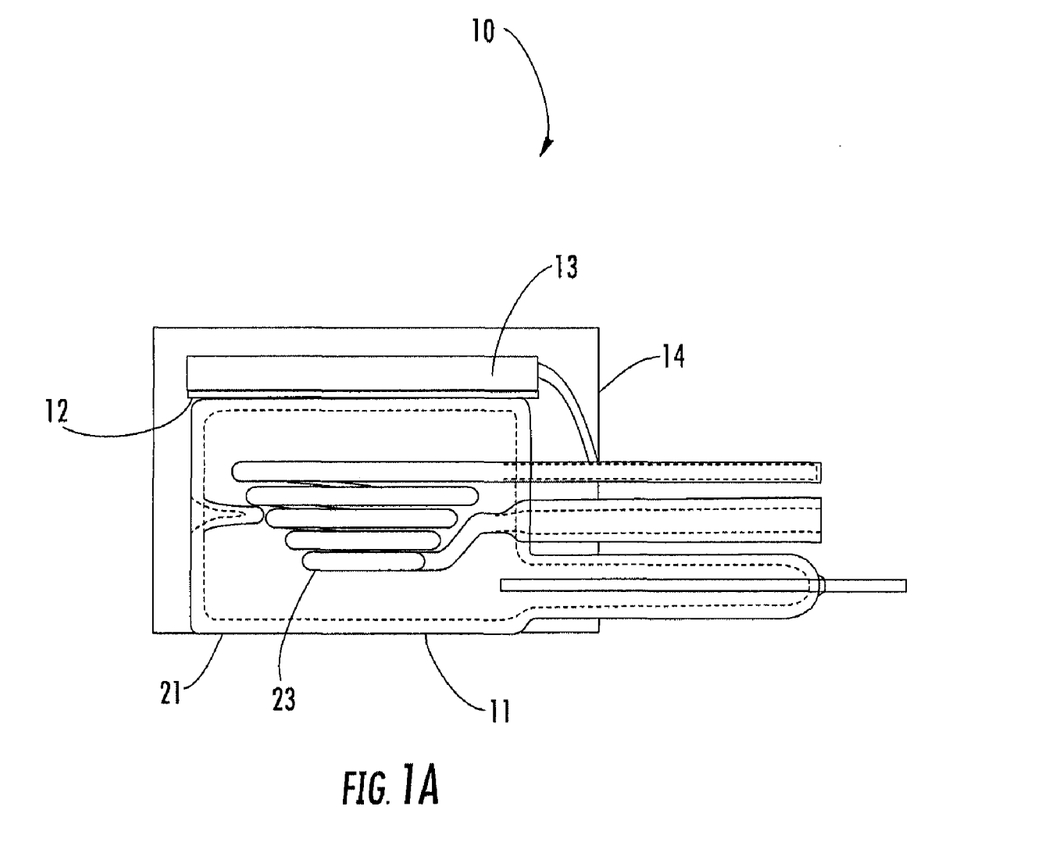
FIG. 1A shows a cross-sectional side view of an embodiment of a bulb assembly according to the present invention.
Figure 1B:
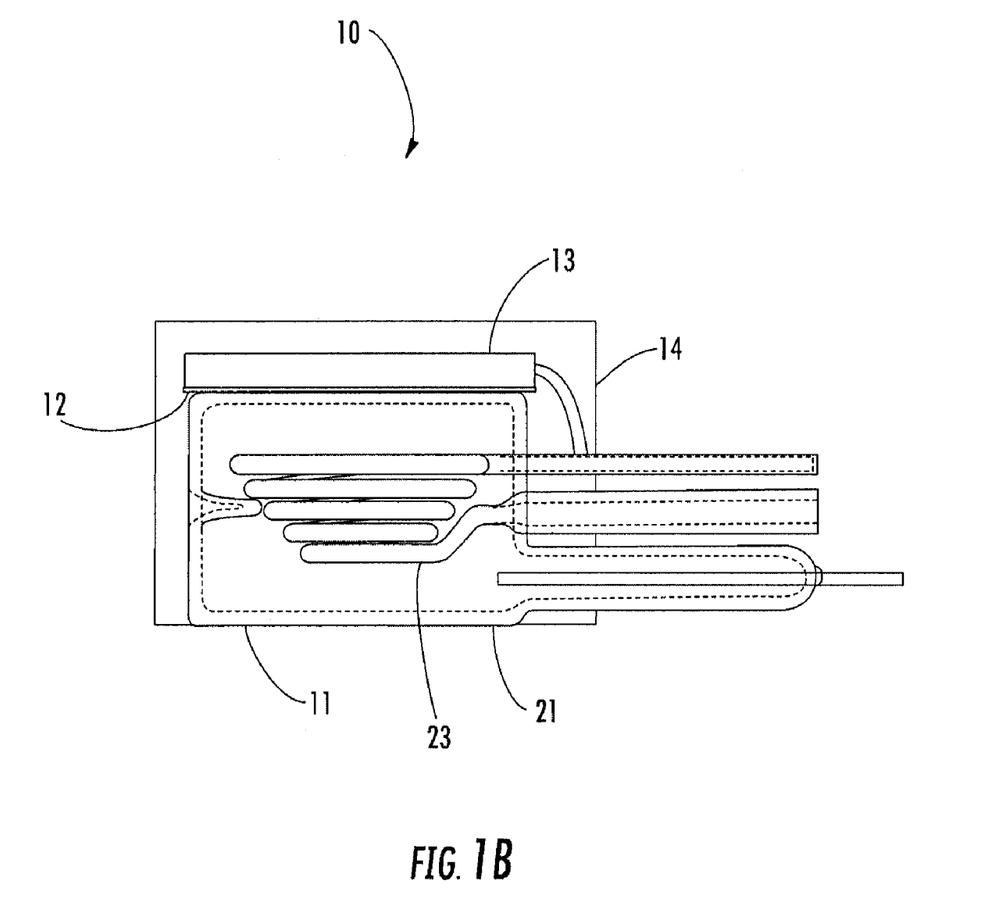
FIG. 1B shows a cross-sectional side view of an embodiment of a bulb assembly according to the present invention.

FIGS. 1A-B each shows a cross-sectional view of an embodiment of bulb assembly 10 according to the present invention. In each embodiment shown in FIGS. 1A-B, bulb assembly 10 comprises bulb 11, reflector 12, coil 13, and housing 14. Bulb 11 comprises vortex tube 23, as shown. The view shown in FIG. 1A is of an embodiment of bulb 11 wherein vortex tube 23 is constructed with a right-hand (clockwise) spiral. The view shown in FIG. 1B is of an embodiment of bulb 11 wherein vortex tube 23 is constructed with a left-hand (counter-clockwise) spiral.

Figure 2A:
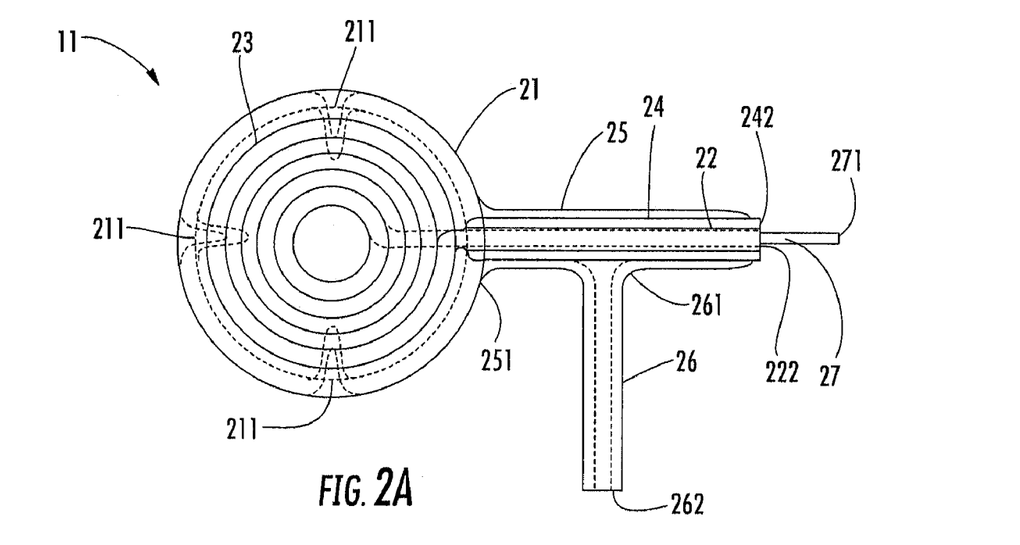
FIG. 2A shows a top view of an embodiment of a bulb according to the present invention.
Figure 2B:
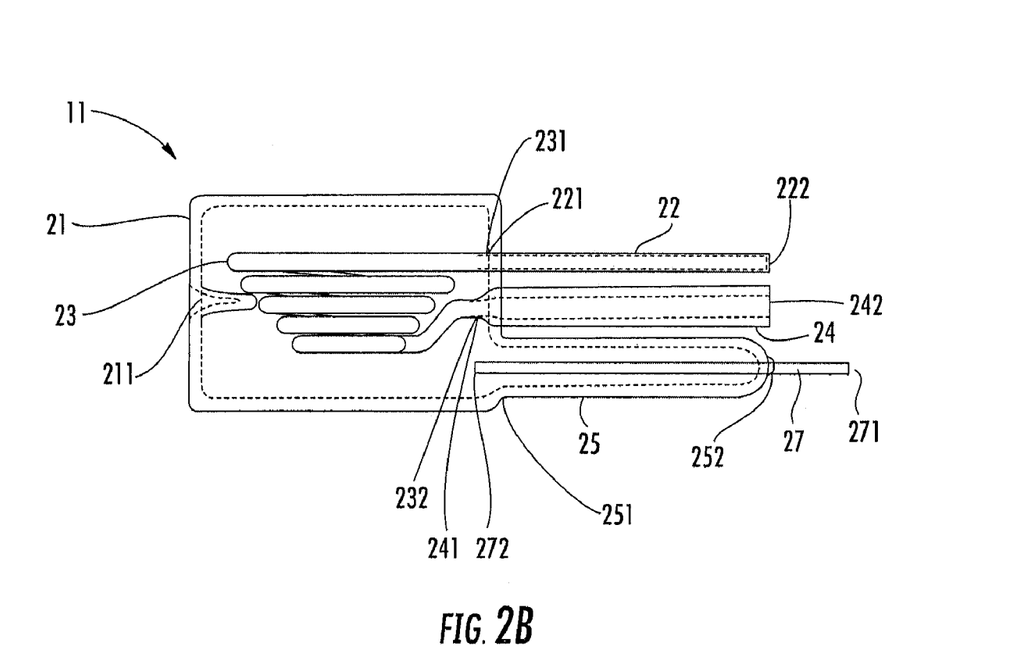
FIG. 2B shows a cross-sectional side view of an embodiment of a bulb according to the present invention.
Figure 2C:
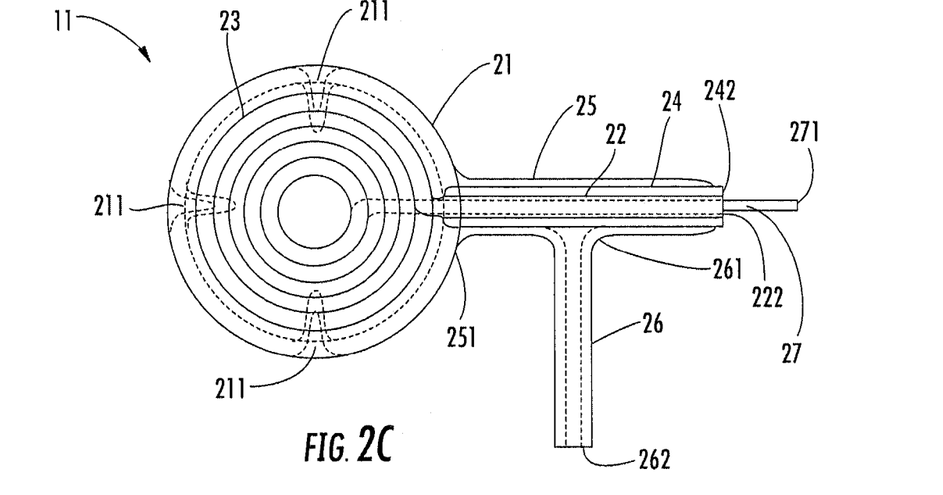
FIG. 2C shows a top view of an embodiment of a bulb according to the present invention.
Figure 2D:
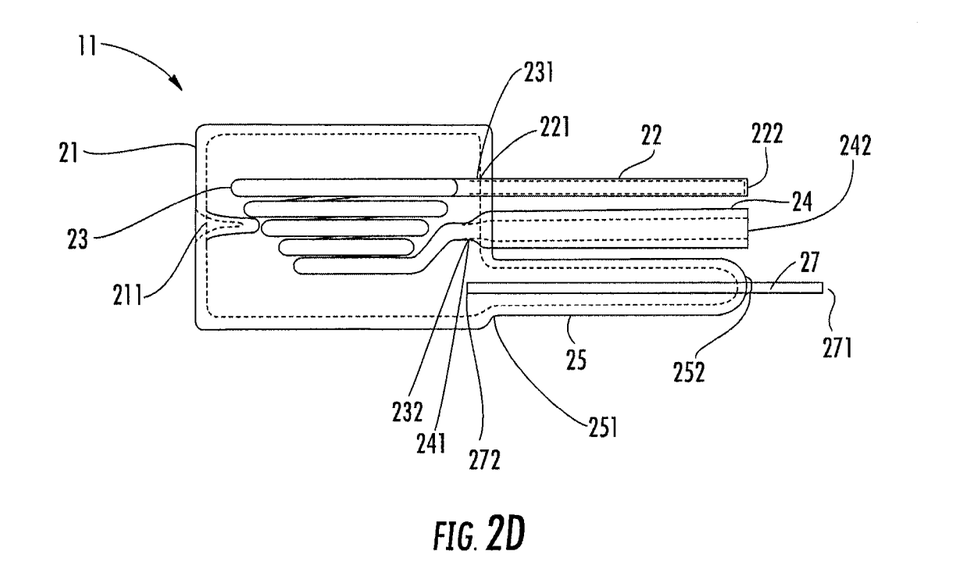
FIG. 2D shows a cross-sectional side view of an embodiment of a bulb according to the present invention.

FIGS. 2A-D show embodiments of bulb 11 according to the present invention. FIG. 2A shows a top view of an embodiment of bulb 11 wherein vortex tube 23 is constructed with a right-hand spiral. FIG. 2B shows a cross-sectional view of the embodiment of bulb 11 shown in FIG. 2A. FIG. 2C shows a top view of an embodiment of bulb 11 wherein vortex tube 23 is constructed with a left-hand spiral. FIG. 2D shows a cross-sectional view of the embodiment of bulb 11 shown in FIG. 2C.

Each embodiment of bulb 11 shown in FIGS. 2A-D comprises shell 21, inlet tube 22, vortex tube 23, outlet tube 24, electrode enclosure 25, fill port 26, and electrode 27. According to the present invention, shell 21 has a hollow interior and may be constructed of one of many rigid, gas-impermeable, nonconductive materials. In an embodiment of bulb 11 of the present invention, shell 21 is constructed of glass using fabrication techniques known in the glass-forming art. Shell 21 may be transparent, translucent, or opaque. In an implementation of this embodiment, the outer surface of shell 21 comprises the outer surfaces of inlet tube 22, outlet tube 24, and electrode enclosure 25. Shell 21 may be formed to include one or more indentations 211. Such indentations aid in supporting vortex tube 23 during handling and operation of bulb assembly 10.

Inlet tube 22 comprises a hollow tube of a rigid, gas-impermeable, nonconductive material (such as, for example, glass), and has a first open end 221 and a second open end 222 and a hollow interior communicating between first open end 221 and second open end 222. Likewise, outlet tube 24 comprises a hollow tube of a rigid, gas-impermeable, nonconductive material (such as, for example, glass), and has a first open end 241 and a second open end 242 and a hollow interior communicating between first open end 241 and second open end 242.

Figure 4A:
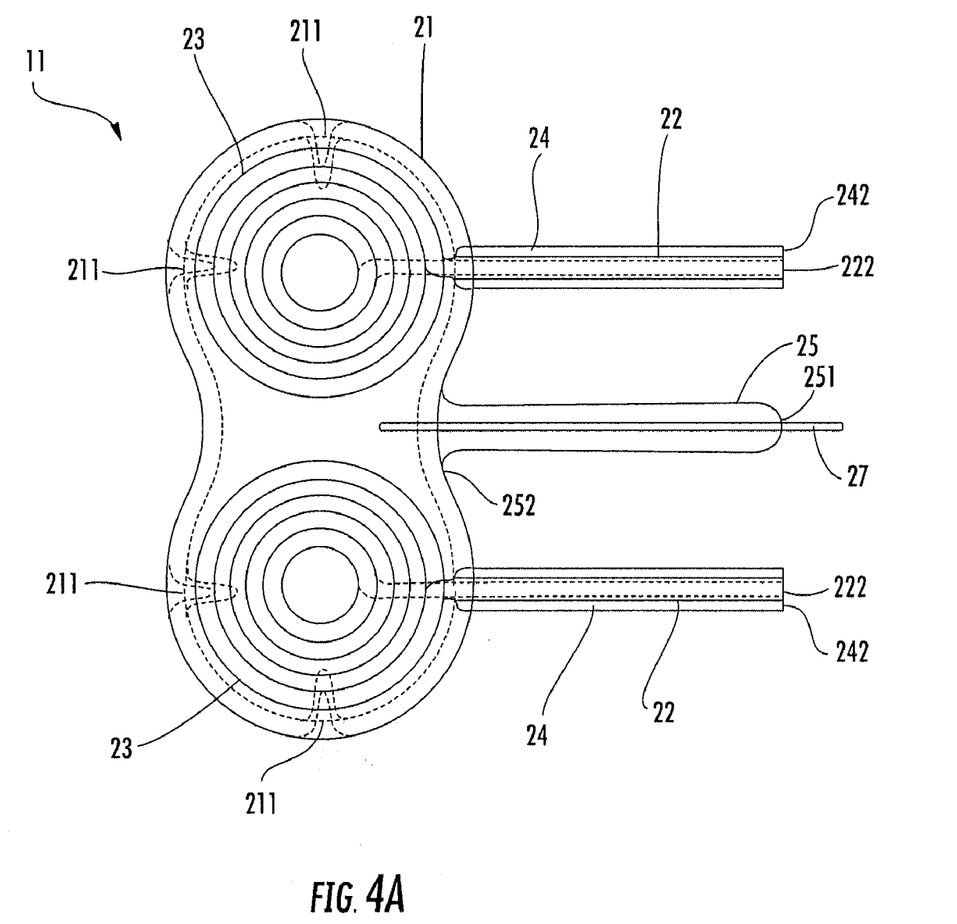
FIG. 4A shows a top view of an embodiment of a bulb according to the present invention.
Figure 4B:
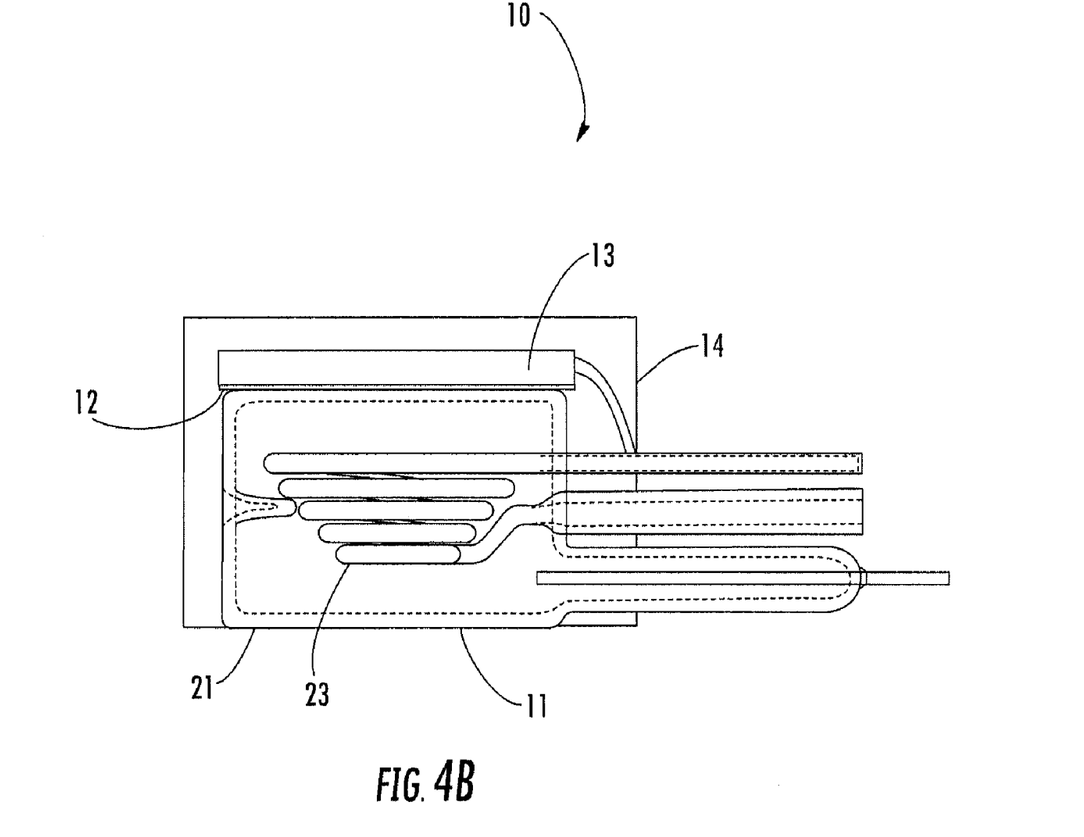
FIG. 4B shows a cross-sectional side view of an embodiment of a bulb assembly according to the present invention.
Figure 4C:
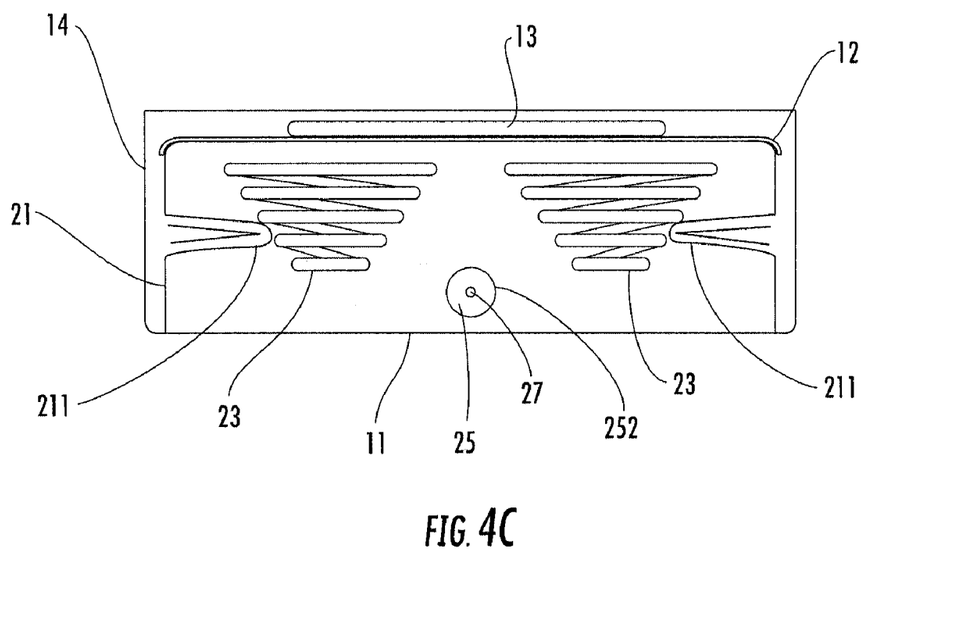
FIG. 4C shows a partially cutaway end view of an embodiment of a bulb assembly according to the present invention.

Vortex tube 23 comprises a hollow tube of a rigid, gas-impermeable, nonconductive material (such as, for example, glass), formed into a concentric spiral and having a first open end 231 and a second open end 232. The hollow interior of vortex 23 communicates between first open end 231 and second open end 232. According to an embodiment of the present invention, the spiral of vortex tube 23 comprises three or more turns. Preferably, vortex tube 23 comprises a prime number of turns, but this is not required. The turns of vortex tube 23 are concentric and decrease in diameter between first open end 231 and second open end 232 such that vortex tube 23 takes on a conical appearance. As mentioned previously herein, vortex tube 23 may be constructed with either a right-hand or left-hand spiral. It is preferred that two bulb assemblies, one comprising a right-hand spiral and the other comprising a left-hand spiral, are used in tandem to enhance the effects of the present invention, but this is not required. In an alternate embodiment of bulb 11 according to the present invention (as shown in FIGS. 4A-C), two vortex tubes 23, one comprising a right-hand spiral and the other comprising a left-hand spiral, are enclosed within a single shell 21. Each vortex tube 23 has its own inlet tube 22 and outlet tube 24 in this embodiment.

First open end 231 of vortex tube 23 is airtightly engaged with first open end 221 of inlet tube 22 (as used herein, the terms "airtight" and "gas-impermeable" have the same meaning unless otherwise indicated). Second open end 232 of vortex tube 23 is airtightly engaged with first open end 241 of outlet tube 24. Accordingly, inlet tube 22, vortex tube 23, and outlet tube 24 form a conduit. The hollow interior of inlet tube 22 communicates with the hollow interior of outlet tube 24 through the hollow interior of vortex tube 23.

The inner diameters of inlet tube 22, vortex tube 23, and outlet tube 24 are sized in relation to the material that will be moved therethrough. Accordingly, the inner diameters of inlet tube 22, vortex tube 23, and outlet tube 24 will be narrower in an implementation of bulb assembly 10 of the present invention wherein a gas will be moved through the conduit formed by inlet tube 22, vortex tube 23, and outlet tube 24. The inner diameters of inlet tube 22, vortex tube 23, and outlet tube 24 will be wider in an implementation of bulb assembly 10 of the present invention wherein a liquid will be moved through the conduit formed by inlet tube 22, vortex tube 23, and outlet tube 24. Typically, inlet tube 22, vortex tube 23, and outlet tube 24 have substantially the same inner diameter. Optionally, the inner diameter of outlet tube 24 may be greater than the inner diameter of vortex tube 23, to permit efficient outflow of material from vortex tube 23.

The outer surface of vortex tube 23 adjacent to first open end 231 is airtightly joined with the inner surface of shell 21, as is the outer surface of vortex tube 23 adjacent to second open end 232. Thus, a material inside vortex tube 23 is precluded from intermixing with a material that is outside vortex tube 23 but within shell 21. In an embodiment of bulb 11, the outer surface of vortex tube 23 adjacent to first open end 231 is integral with the inner surface of shell 21, as is the outer surface of vortex tube 23 adjacent to second open end 232.

Electrode enclosure 25 of bulb 11 comprises a hollow tube of a rigid, gas-impermeable, nonconductive material (such as, for example, glass), and has first end 251 and second end 252. First end 251 of electrode enclosure 25 is open and communicates with the interior of shell 21. A gas-impermeable seal exists between first end 251 and shell 21. In an embodiment of bulb 11, first end 251 is integral with shell 21. Second end 252 of electrode enclosure 25 forms a gas-impermeable seal around electrode 27.

Fill port 26 comprises a hollow tube of a rigid, gas-impermeable, nonconductive material (such as, for example, glass), and has first end 261 and a second end 262 and a hollow interior communicating between first end 261 and second end 262. First end 261 of fill port 26 communicates with the interior of shell 21. In an embodiment of bulb 11, first end 261 of fill port 26 communicates with the interior of shell 21 through electrode enclosure 25. In an embodiment of bulb 11, first end 261 is integral with electrode enclosure 25. Fill port 26 is used to fill shell 21 (including electrode enclosure 25) with gas. After shell 21 is filled, second end 262 of fill port 26 is truncated and sealed.

In an embodiment, shell 21 is filled with a gas mixture comprising about 75% argon and about 25% neon. In an embodiment, shell 21 is filled with a gas mixture comprising about 60% argon and about 40% neon. In an embodiment, shell 21 is filled with a gas mixture comprising about 75% neon and about 25% argon. In an embodiment, shell 21 is filled with a gas mixture comprising about 60% neon and about 40% argon. In an embodiment, shell 21 is filled with a gas mixture comprising about 20% argon, about 5% krypton, about 5% xenon, about 10% helium, and about 60% neon. In an embodiment, shell 21 is filled with a gas mixture comprising about 20% neon, about 20% argon, about 20% krypton, about 10% helium, and about 30% xenon. In an embodiment, shell 21 is filled with a gas mixture comprising about 65% xenon, about 25% argon, and about 10% krypton. In an embodiment, shell 21 is filled with a gas mixture comprising about 10% xenon, about 15% argon, about 65% krypton, and about 10% helium. In an embodiment, shell 21 is filled with a gas mixture comprising about 50% argon, about 10% neon, about 25% krypton, about 10% xenon, and about 5% helium. In an embodiment, the gas mixture is pressurized to a pressure between about 2 Torr and about 25 Torr. In an embodiment, the noble gas mixture is pressurized to a pressure of about 7

Ton. However, other noble gas mixtures and pressures may be used and are within the scope of the present invention.

Electrode 27 is comprised of Kovar or another conductive material known in the art that is capable of withstanding the thermal and electrical stresses to which it is subject during operation of the present invention (discussed hereinafter). Electrode 27 comprises first end 271 which terminates in the hollow interior of shell 21, and second end 272 which extends through the gas-impermeable seal formed by closed end 252 of electrode enclosure 25.

Referring back to FIG. 1, reflector 12 comprises a reflective material of a type known in the art capable of reflecting visible and non-visible radiation. In one implementation, reflector 12 is constructed of a reflective Mylar, although other suitable materials may be used and are contemplated to be within the scope of the present invention. The reflective side of reflector 12 faces bulb 11. Reflector 11 must be selected and oriented so that it reflects the photons produced inside shell 21, but does not reflect the electromagnetic waves produced by coil 13.

Figure 3:
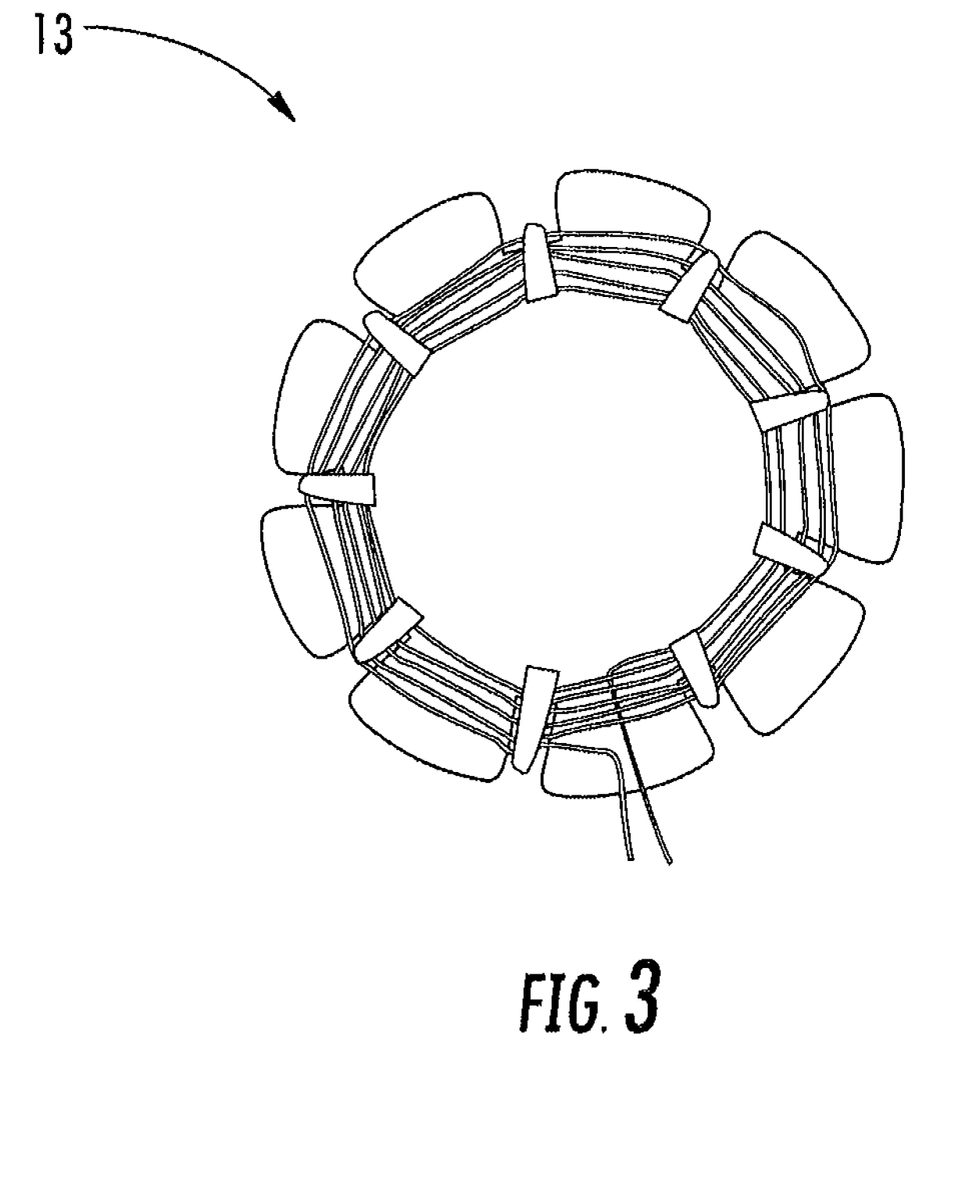
FIG. 3 shows a top view of an embodiment of a bucking coil used in a bulb assembly according to the present invention.

Coil 13 shown in FIG. 1 comprises a bucking coil of a type known in the art. In an embodiment shown in FIG. 3, coil 13 comprises a 9-slot spider web coil having ten windings. However, other configurations of coil 13 may be used at the discretion of a practitioner of the present invention if different electromagnetic performance characteristics are desired. A spider web coil is preferred over other coil arrangements because it provides low inductance, and also creates collapsing electromagnetic fields because of its overlapping windings. Other coil configurations may be used within the scope of the present invention, such as, for example, a basket weave coil, a Mobius Coil, a Cadeusus coil, or any other coil configuration that would produce a Tesla Longitudinal Wave (i.e., a non-hertzian wave). As shown in FIG. 1, coil 13 is positioned such that reflector 12 is between coil 13 and bulb 11.

Housing 14 shown in FIG. 1 comprises any form of electrical assembly packaging known in the art that is suitable for the materials and properties of bulb assembly 10 as described herein.

In operation of bulb assembly 10 according to an embodiment of the present invention, the following events are occurring simultaneously:

1. A material is caused to flow into inlet tube 22, through vortex tube 23, and out of outlet tube 24. The material used in a particular implementation the present invention may be selected at the discretion of the practitioner. The only constraint on the material is that it be able to flow through vortex tube 23. In one implementation of the present invention, the material flowing through vortex tube 23 comprises ozone, but the material does not necessarily have to be ozone or a gas. The molecules of the material traveling through vortex tube 23 become accelerated as the diameter of the turns in vortex tube 23 decrease. In addition, the spiral path followed by the molecules of the material traveling through vortex tube 23 induces a "spin" to the molecules, causing the molecules to rotate in the direction of the vortex tube 23 spiral. The acceleration and spin "excite" the molecules, and the effect of the acceleration and spin are exploited by the present invention, as further discussed hereinafter.

2. An RF signal is transmitted through coil 13. While the parameters of the RF signal transmitted through coil 13 are left to the discretion of the practitioner in a particular implementation the present invention, the parameters must be selected to operate in conjunction with the parameters of coil 13 to produce the desired output of bulb assembly 10 (discussed hereinafter). In one implementation of the present invention where coil 13 comprises a 9-slot spider web coil having ten windings, coil 13 is energized by a carrier signal of approximately 27.5 MHz that transmits electromagnetic radiation at a power of about 25 watts. Other frequency ranges and coil configurations may be used in other embodiments of the present invention. Also, a pulsating direct current can be used in an embodiment of the present invention. Twice per cycle, the carrier signal of coil 13 is at a state where there is no electric field ("E field") or magnetic field ("B field") present. Both the E field and B field measurements are 0. However, in this state there is both an electric potential "V" and a magnetic potential "A" present. Neither electric potential V nor magnetic potential A are readily measurable with known instrumentation. However, the effect of such potentials on charges has been demonstrated through experimentation, such as by Yoseph Imry and Richard A. Webb, in "Quantum Interference and the Aharonov-Bohm Effect," Scientific American, April 1989, at 56, the disclosure of which is incorporated herein by reference.

3. A pulsed DC voltage is applied to electrode 27. While the voltage applied to electrode 27 is left to the discretion of the practitioner in a particular implementation of the present invention, the voltage must be sufficient to cause electrical arcing between electrode 27 and the noble gas molecules inside shell 21, and must be selected to operate in conjunction with the material flowing through vortex tube 23 and the fields and potentials created by the energization of coil 13, to produce the desired output of bulb assembly 10 (discussed hereinafter). In one implementation of the present invention, electrode 27 is energized by a pulsed DC voltage (with at least one pulse per second) selected from the range of voltages between about 20 KVDC and about 50 KVDC. Voltages outside this range also are within the scope of the present invention. The arcing between electrode 27 and the noble gas molecules inside shell 21 "excites" the noble gas molecules, producing photons (both visible and invisible). In an alternative embodiment of the present invention, an appropriately selected RF signal is used to excite the noble gas molecules in addition to, or in lieu of, the pulsed DC voltage.

It is accepted in the art of quantum mechanics that a photon possesses quantum information about the atom from which it was produced. While inside bulb assembly 10, a photon produced from the excited noble gas molecules inside shell 21 interacts with both the molecules moving through vortex tube 23 and with the electric potential V and magnetic potential A produced by coil 13. Through such interaction, the quantum information possessed by the photon is altered. Most notably, the photon acquires quantum information about the molecules inside vortex tube 23. When the photon is emitted from bulb assembly 10 into a target subject matter, the complex quantum information possessed by the photon is transferred to the target subject matter as well. Thus, for example, where the target subject matter is a human body, through placement of bulb assembly 10 of the present invention in proximity to the human body, it is possible to transmit the benefits of certain medicines or other substances into a patient's body, without requiring the patient to ingest the medicine. The medicine or other substance is caused to flow through vortex tube 23. The photons generated by electrode 27 obtain beneficial quantum information about the medicine as the photons interact with the molecules moving through vortex tube 23. The photons emitted by bulb assembly 10 possess the quantum information of the medicine or other substance. If bulb assembly 10 is placed in proximity to the patient's body, the emitted photons enter the patient's body. Inside the patient's body, the photons interact with the patient's cells, delivering the beneficial quantum information of the medicine or other substance directly to the patient's cells.

In another embodiment of the present invention, the medicine or other substance is placed between bulb assembly 10 and the patient's body before bulb assembly 10 is placed in proximity to the patient's body. The photons emitted by bulb assembly 10 obtain the quantum information of the medicine or other substance, and then the emitted photons enter the patient's body. Inside the patient's body, the photons interact with the patient's cells, delivering the beneficial quantum information of the medicine or other substance directly to the patient's cells. In this embodiment of the present invention, another substance may or may not be flowing through vortex tube 23 when bulb assembly 10 is placed in proximity to the patient's body.

In addition to altering the quantum information possessed by the photons, the operation of bulb assembly 10 also affects the molecular properties of the material flowing through vortex tube 23. The interaction of the photons, the molecules moving through vortex tube 23, and the electric potential V and magnetic potential A produced by coil 13, alters the energy possessed by the molecules.

Optionally, one or more additional electromagnetic waveforms may be introduced into the noble gas mixture through electrode 27 and/or coil 13. While the parameters of such electromagnetic waveforms introduced are left to the discretion of the practitioner in a particular implementation of the present invention, the parameters must be selected to operate in conjunction with the material flowing through vortex tube 23, the fields and potentials created by the energization of coil 13, and the pulsed DC voltage applied to electrode 27, to produce the desired energetic output. In one exemplary implementation of the present invention, a square waveform having a frequency selected from the range of frequencies between about 600 Hz and about 800 Hz is introduced through electrode 27. The frequency is "imprinted" on the photons, altering the photons' quantum information. Likewise, the molecules of the material flowing through vortex tube 23 are imprinted with the introduced frequency.

It is accepted in the quantum mechanics art that consecutive photons emitted from a single photon source have the same quantum information and, thus, will to be able to interfere in a very peculiar way, as long as they are in the same, single mode. Photons are characterized by several physical properties, such as their frequency and polarization, and together these properties define the "mode" of the electromagnetic field with which the photon is associated. In the simplest approach, a mode can be regarded as a polarized, monochromatic, plane wave, but it can also be defined in a much more flexible way: the photon can be spread coherently over several modes, defining a new single mode.

If two photons are in the same mode, quantum mechanics predicts that a bunching, or a coalesce effect occurs. When the noble gas molecules inside shell 21 are excited and photons are created, the photons have a 50/50 chance of being reflected off of reflector 12 or transmitted. Assuming that one photon that is being transmitted ends up in exactly the same mode as another photon being reflected. In other words, all of the properties of the two photons are identical at the point of output, so that they become essentially indistinguishable. In that case there are four possible combinations for the two photons being transmitted or reflected: (1) one photon may be transmitted and the other reflected; (2) both photons may be transmitted; (3) both photons may be reflected; or (4) the photons may coalesce. The coalescence is accomplished by the quantum interference (wave packet) which is contributed by coil 13.

As is usual in quantum mechanics, there is a probability amplitude for each of these configurations, and the transmission or reflection probabilities are given by the square of the modulus of the sum of these amplitudes. According to this simple calculation, two amplitudes have opposite signs, and so cancel each other, i.e., they interfere destructively. The result is that the two photons must go to the same output beam. It is as though they coalesce as they meet at the point of excitation.

This quantum-interference effect, which can be attributed to the "basonic" character of photons, was first predicted and observed in 1987. See C. K. Hong, Z. Y. Ou, and L. Mandel, *Phys. Rev. Lett.* 59, at 2044-2047 (1987), the disclosure of which is incorporated herein by this reference. There, pairs of "twin photons" produced simultaneously in a process called parametric down conversion which can be induced by shining laser light into a crystal. An optical delay was added to the path of one of the two photons. If this delay is not 0, each one of the "twin photons" is randomly transmitted and reflected, i.e., they miss each other. But if the delay is exactly 0, which is the case in the present invention, the photons overlap and the coalescence effect occurs.

This coalescence is not just a curious quantum effect, but has fundamental implications in the field of quantum information processing and delivery. This quantum photonic network is based on indistinguishable single photons carrying quantum information from mode to mode as explained above. Electrode 27 produces photons that are spread incoherently over many modes, but the electric and magnetic potentials produced by coil 13 and the energy pushing and reflecting the many photons produced, provides an adequate amount for single mode behavior.

The imprinting of quantum information onto the photons produced by bulb assembly 10 is created by a Rabi flopping effect of a two level, quantum mechanical system. The two levels are two energy levels of the noble gas molecules, and the two orientations of the spin of the two bulb assemblies (left-hand and right-hand) counter to each other. In addition, ordinary transverse electromagnetic waves (created by the bulb ignition field) are coupled with a Tesla (non-hertzian) Longitudinal Wave (product of cancellation fields from the coil).

Non-hertzian electromagnetics are the quantum mechanical effects and influences that can be produced by electrical and magnetic potentials in regions where the E field and B field both are 0. The Aharonov-Bohm effect shows that while the E and the B fields remain at 0, electrical and magnetic potentials exist and cause physical effects. When the E and B fields are 0, there are no physical results observed because there is no physical energy flow. However, when E and B fields are 0, under certain conditions (as described herein) their sources (and their scalar electric potential V and magnetic potential A) can produce physical consequences. Because there is no energy transferred to objects when the electric and magnetic fields collapse to 0, scalar electric potential V and magnetic potential A are decoupled from E and B fields and become scalar potentials which permeate all objects and transfer quantum information instantaneously. This makes detecting electric potential V and magnetic potential A virtually impossible with currently available instrumentation.

Transport of ions across membranes and against a thermodynamic gradient is essential to many biological processes.

Synthetics that transport metal ions across lipid or liquid membranes are well known. In the case of the present invention, light is used to facilitate transport of quantum information piggybacked on the scalar potentials generated by bulb assembly 10. Thermodynamic driving forces are provided by ion concentration difference between the material inside vortex tube 23 and the excited noble gases inside shell 21, coupled with the photo modulation of the RF carrier by an asymmetric photon flux. Active transport is induced by electron transfer in a photoactive molecule that is asymmetrically disposed across a lipid bilayer. The present invention comprises a synthetic, light driven transmembrane pump based on a binding shuttle molecule whose function is powered by an intramembrane artificial photosynthetic reaction center. The resulting structure transports quantum information of a material moving through vortex 23 across the bilayer of a liposome to develop both an ion concentration gradient and a membrane potential. Although the quantum yield is relatively low, the electrochemical potential developed in a target subject matter (such as, for example, a biological system) can be significant.

Embodiments of the present invention may be adapted for a specific ailment. For example, embodiments of the present invention may be adapted for the treatment of, or symptom reduction in, connective tissue disorders such as, for example, lymphedma, as well as for the treatment of, or symptom reduction in, ailments such as lymphoma, breast cancer, chronic pain, ecchymosis, hematoma, infections, prostate cancer, benign prostatic hyperplasia, mastodynia, edema, dental diseases and inflammation, colitis, varicose veins, clogged arteries, leg and back pain, sciatica, arthritis, carpel tunnel syndrome, scars, cellulite, fibromyalgia, lupus, and other ailments. Such embodiments of the present invention can be used in combination with other medical protocols.

As discussed herein, many parameters of the present invention are adaptable including, for example, the material selected to flowing through vortex tube 23, the number of turns in vortex tube 23, the gas mixture within shell 21, the frequency of the signal transmitted through coil 13, the voltage used to excite the gas molecules within shell 21.

Although the present invention may be adapted for a specific ailment, such adaptation is not required. The present invention transfers quantum information using scalar potentials combined with an accelerated material moving through vortex tube 23 that produces energy to be transferred to the target subject matter. If, for instance, the target site is a biological system that contains disorganized protein structures (i.e., ionized or loosely coupled protein structures), the energy transferred to the target site interacts with the site and the disorganized protein commences to disassociate, with normal function restored. If a gas (e.g., ozone) is moved through vortex tube 23, biological effects are observed that normally are seen when one insufflates or infuses the ozone into the biological system. If a material is moved through vortex tube 23, a reduction in the rate of degradation of the material is observed.

The present invention (including scalar potentials, spiral vortex tube, noble gases, and specialized frequencies) provides both a method for transmitting the quantum information of a material moving through vortex 23 into a target subject matter, and also a method for binding or strengthening the bond of the material moving through vortex tube 23, which results in a slowing down of a standard degradation process of that material. If the emitted photons are directed at a biological system, it aids the biological system in healing itself. For a biological system, the system is delivering energy and quantum information for the biological system to use at its own discretion.

While this invention has been described as having a preferred design, the present invention can be further modified within the scope and spirit of this disclosure. This application is therefore intended to cover any variations, uses, or adaptations of the invention using its general principles. For example, the methods disclosed herein and in the appended claims represent one possible sequence of performing the steps thereof. A practitioner of the present invention may determine in a particular implementation of the present invention that multiple steps of one or more of the disclosed methods may be combinable, or that a different sequence of steps may be employed to accomplish the same results. Each such implementation falls within the scope of the present invention as disclosed herein and in the appended claims. Furthermore, this application is intended to cover such departures from the present disclosure as come within known or customary practice in the art to which this invention pertains.

We claim:

1. A bulb comprising:
a transparent shell enclosing a hollow interior;
an electrode-less tube having a first open end and a second open end and a continuous pathway communicating between said first open end and said second open end, said electrode-less tube intersecting with said shell such that said first open end and said second open end reside outside said shell and a portion of said electrode-less tube between said first open end and said second open end resides within said shell, each said intersection of said electrode-less tube and said shell being accomplished such that any contents of said hollow interior of said shell are sealed within said shell and any contents of said hollow interior of said shell are segregated from any contents of said portion of said electrode-less tube residing within said shell;
at least one electrode, each said at least one electrode having first and second electrode ends, wherein said first electrode end of each said at least one electrode terminates within said shell and said second electrode end of each said at least one electrode terminates outside said shell, said shell forming a gas-impermeable seal around said at least one electrode, wherein said at least one electrode is not in contact with any contents of said electrode-less tube; and
a source of electromagnetic waves, said source of electromagnetic waves positioned such that electromagnetic waves emanating from said source of electromagnetic waves pass through said shell, wherein said source of electromagnetic waves comprises a bucking coil.

2. The bulb of claim 1, wherein said portion of said electrode-less tube residing within said shell is configured as a spiral comprising a plurality of concentric turns.

3. The bulb of claim 2, wherein each successive concentric turn of said plurality of concentric turns decreases in diameter.

4. The bulb of claim 2, wherein said spiral comprises three or more concentric turns.

5. The bulb of claim 2, wherein said spiral comprises a prime number of concentric turns.

6. The bulb of claim 1, wherein said hollow interior of said shell comprises gaseous matter.

7. The bulb of claim 6, wherein said gaseous matter comprises a mixture of noble gasses.

8. The bulb of claim 7, wherein said mixture of noble gasses comprises xenon.

9. The bulb of claim 7, wherein said mixture of noble gasses comprises argon.

10. The bulb of claim 7, wherein said mixture of noble gasses comprises krypton.

11. The bulb of claim 7, wherein said mixture of noble gasses comprises neon.

12. The bulb of claim 7, wherein said mixture of noble gasses comprises helium.

13. The bulb of claim 1, wherein said portion of said electrode-less tube residing within said shell encloses a flowing substance.

14. The bulb of claim 13, wherein the hollow interior of said shell outside said electrode-less tube contains a gaseous matter, and wherein said flowing substance does not intermingle with said gaseous matter.

15. The bulb of claim 13, wherein said flowing substance comprises a gaseous substance.

16. The bulb of claim 15, wherein said gaseous substance comprises ozone.

17. The bulb of claim 13, wherein said flowing substance comprises a substance used to treat an ailment suffered by a biological system.

18. The bulb of claim 13, wherein said flowing substance comprises a medicine.

19. A bulb comprising:

a transparent shell enclosing a hollow interior;

an electrode-less tube having a first open end and a second open end and a continuous pathway communicating between said first open end and said second open end, said electrode-less tube intersecting with said shell such that said first open end and said second open end reside outside said shell and a portion of said electrode-less tube between said first open end and said second open end resides within said shell, each said intersection of said electrode-less tube and said shell being accomplished such that any contents of said hollow interior of said shell are sealed within said shell and any contents of said hollow interior of said shell are segregated from any contents of said portion of said electrode-less tube residing within said shell;

at least one electrode, each said at least one electrode having first and second electrode ends, wherein said first electrode end of each said at least one electrode terminates within said shell and said second electrode end of each said at least one electrode terminates outside said shell said shell forming a gas-impermeable seal around said at least one electrode, wherein said at least one electrode is not in contact with any contents of said electrode-less tube; and a source of electromagnetic waves, said source of electromagnetic waves positioned such that electromagnetic waves emanating from said source of electromagnetic waves pass through said shell, wherein said portion of said tube residing within said shell encloses a flowing substance, said source of electromagnetic waves is energized by an alternating electrical current, and a voltage is applied to said electrode.

* * * * *